US012582777B2

(12) United States Patent
Yin et al.

(10) Patent No.: US 12,582,777 B2
(45) Date of Patent: Mar. 24, 2026

(54) METHOD OF MANUFACTURING A SUB-ASSEMBLY OF A MEDICAMENT DELIVERY DEVICE

(71) Applicant: SHL Medical AG, Zug (CH)

(72) Inventors: Ming-Ting Yin, Taoyuan City (TW); Philipp Zingel, Taoyuan City (TW); Roman Käslin, Zurich (CH); Lino Manuel Heckhorn Ghilardi, Zurich (CH)

(73) Assignee: SHL Medical AG, Zug (CH)

( * ) Notice: Subject to any disclaimer, the term of this patent is extended or adjusted under 35 U.S.C. 154(b) by 72 days.

(21) Appl. No.: 18/293,929

(22) PCT Filed: Aug. 3, 2022

(86) PCT No.: PCT/EP2022/071828
§ 371 (c)(1),
(2) Date: Jan. 31, 2024

(87) PCT Pub. No.: WO2023/016891
PCT Pub. Date: Feb. 16, 2023

(65) Prior Publication Data
US 2024/0335612 A1     Oct. 10, 2024

(30) Foreign Application Priority Data
Aug. 9, 2021    (EP) ..................................... 21190457

(51) Int. Cl.
*A61M 5/20*          (2006.01)
*A61M 5/315*         (2006.01)
(52) U.S. Cl.
CPC .............. *A61M 5/315* (2013.01); *A61M 5/20* (2013.01); *A61M 2207/00* (2013.01); *A61M 2207/10* (2013.01)

(58) Field of Classification Search
CPC . A61M 5/20; A61M 2207/00; A61M 2207/10
See application file for complete search history.

(56) References Cited

U.S. PATENT DOCUMENTS

| | | | |
|---|---|---|---|
| 5,730,723 A | 3/1998 | Castellano |
| 6,080,130 A | 6/2000 | Castellano |
| | (Continued) | | |

FOREIGN PATENT DOCUMENTS

| | | | |
|---|---|---|---|
| EP | 2620174 B1 | 5/2014 |
| EP | 2675509 B1 | 4/2015 |
| | (Continued) | | |

OTHER PUBLICATIONS

International Search Report and Written Opinion for corresponding PCT application No. PCT/EP2022/071828 dated Nov. 17, 2022.

*Primary Examiner* — Jermie E Cozart
(74) *Attorney, Agent, or Firm* — McDonnell Boehnen Hulbert & Berghoff LLP

(57) ABSTRACT

The present disclosure provides a method of manufacturing a sub-assembly of a medicament delivery device. The method includes identifying one or more standardized components for the sub-assembly of the medicament delivery device from a group of standardized components. The group of standardized components includes at least one of a group of interchangeable plunger rods and a group of interchangeable delivery member guards. The plunger rods in the group have a structural and/or dimensional difference relative to one another, the delivery member guards in the group have a structural and/or dimensional difference relative to one another. The method further includes providing the identified one or more standardized components, providing a universal powerpack for the medicament delivery device, and assembling the sub-assembly of the medicament deliv- (Continued)

ery device using the universal powerpack, and the identified one or more standardized components.

12 Claims, 6 Drawing Sheets

(56)                References Cited

U.S. PATENT DOCUMENTS

| | | | |
|---|---|---|---|
| 6,613,010 | B2 | 9/2003 | Castellano |
| 6,689,095 | B1 | 2/2004 | Garitano |
| 6,824,526 | B2 | 11/2004 | Castellano |
| 7,717,874 | B2 | 5/2010 | Landau |
| 8,647,299 | B2 | 2/2014 | Stamp |
| 8,939,958 | B2 | 1/2015 | Burnell |
| 9,616,175 | B2 | 4/2017 | Bom |
| 9,821,115 | B2 | 11/2017 | Wozencroft |
| 9,884,152 | B2 | 2/2018 | McLoughlin |
| 10,099,013 | B2 | 10/2018 | McLoughlin |
| 10,471,209 | B2 | 11/2019 | Dunne |
| 10,918,803 | B2 | 2/2021 | Kemp |
| 2005/0192530 | A1 | 9/2005 | Castellano |
| 2017/0258998 | A1 | 9/2017 | Stamp |
| 2018/0140781 | A1 | 5/2018 | Kemp |
| 2018/0140782 | A1 | 5/2018 | Kemp |
| 2018/0169338 | A1 | 6/2018 | Mosebach |
| 2019/0167906 | A1 | 6/2019 | Auld |

FOREIGN PATENT DOCUMENTS

| | | | | |
|---|---|---|---|---|
| EP | 1786491 | B1 | 2/2016 | |
| EP | 2968063 | B1 | 8/2017 | |
| EP | 2680906 | B1 | 11/2017 | |
| EP | 2023983 | B1 | 8/2019 | |
| EP | 2781230 | B1 | 8/2019 | |
| EP | 3104909 | B1 | 10/2019 | |
| EP | 3218030 | B1 | 3/2020 | |
| EP | 2204201 | B1 | 4/2020 | |
| EP | 3653241 | A1 | 5/2020 | |
| EP | 3381490 | B1 | 9/2020 | |
| FR | 2905273 | A1 * | 3/2008 | ............. A61M 5/20 |
| WO | 200062846 | A1 | 10/2000 | |
| WO | 2002083211 | A1 | 10/2002 | |
| WO | 2016193355 | A1 | 12/2016 | |
| WO | 2017046556 | A1 | 3/2017 | |
| WO | 2017174668 | A1 | 10/2017 | |
| WO | 2017191159 | A1 | 11/2017 | |
| WO | 2019063267 | A1 | 4/2019 | |
| WO | 2019086372 | A1 | 5/2019 | |
| WO | 2019144048 | A1 | 7/2019 | |
| WO | 2019192971 | A1 | 10/2019 | |
| WO | 2019224782 | A1 | 11/2019 | |
| WO | 2019224783 | A1 | 11/2019 | |
| WO | WO-2019224785 | A1 * | 11/2019 | .......... A61M 5/3157 |
| WO | 2019234134 | A1 | 12/2019 | |
| WO | 2020016313 | A1 | 1/2020 | |
| WO | 2020064572 | A1 | 4/2020 | |
| WO | 2020081480 | A1 | 4/2020 | |
| WO | 2021094047 | A1 | 5/2021 | |

* cited by examiner

Fig. 2A          Fig. 2B

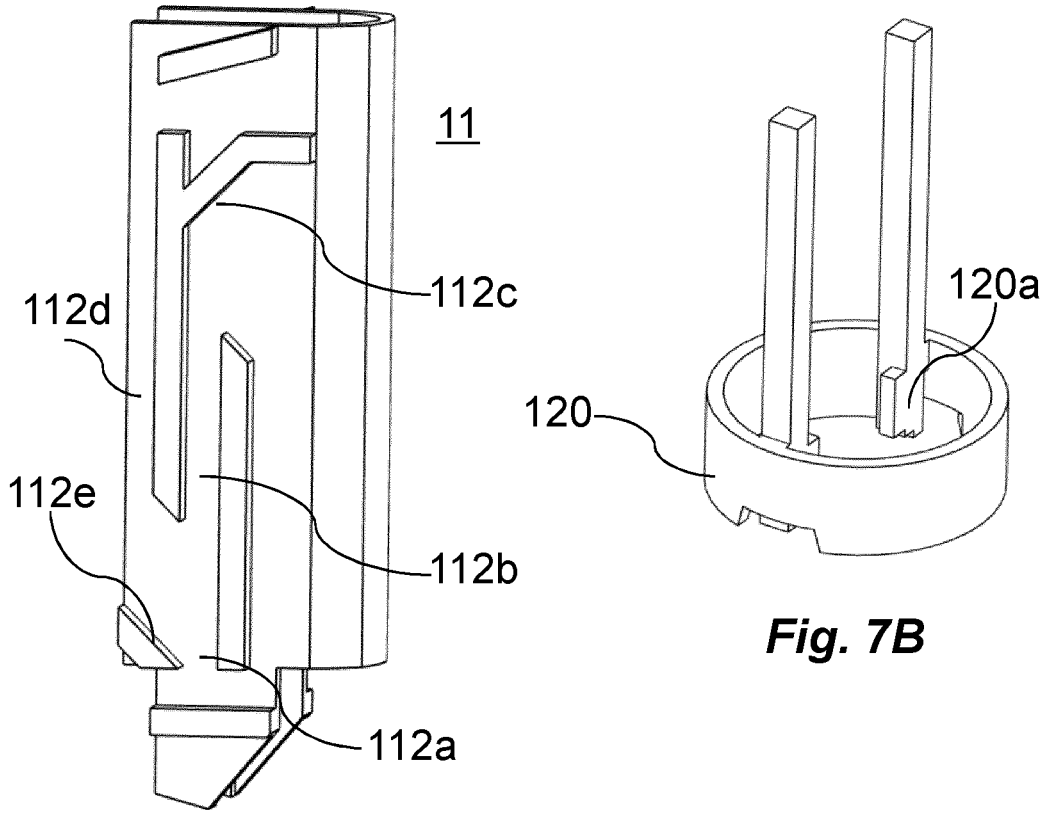
11
112d
112c
112e
112b
112a
Fig. 7A
120
120a
Fig. 7B
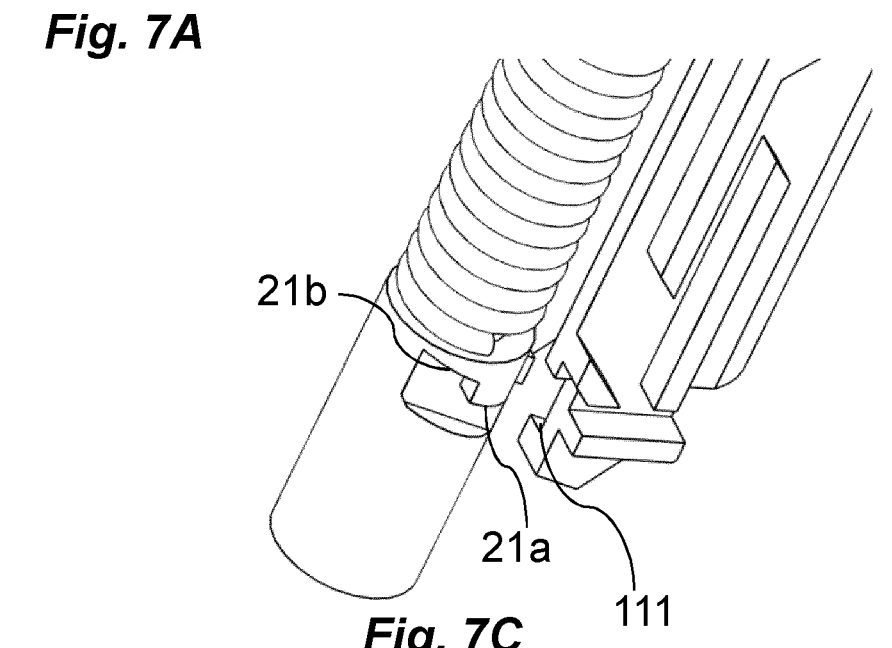
21b
21a
111
Fig. 7C

8'

81'   83a

82a

82b

8'

83b

81b

810b

81a

810a

811a

81c

810c

600
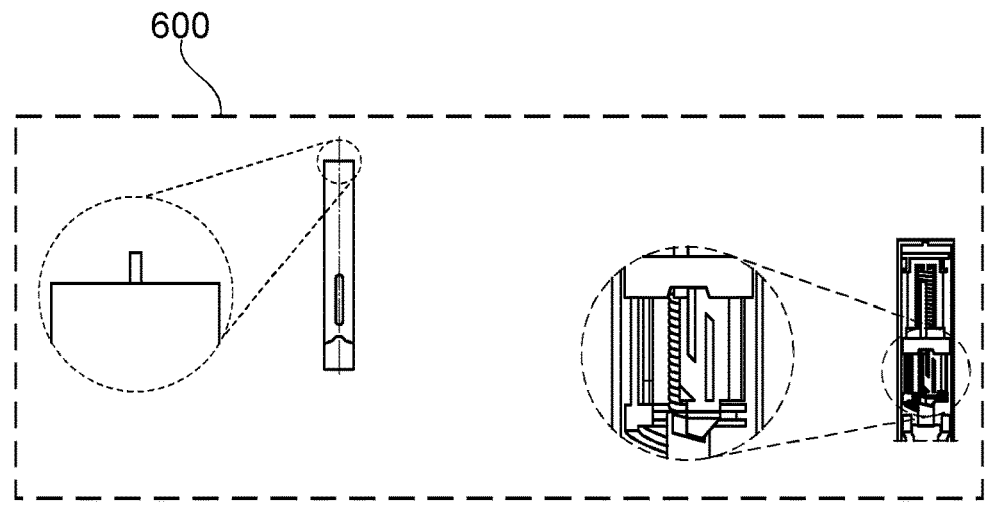
700
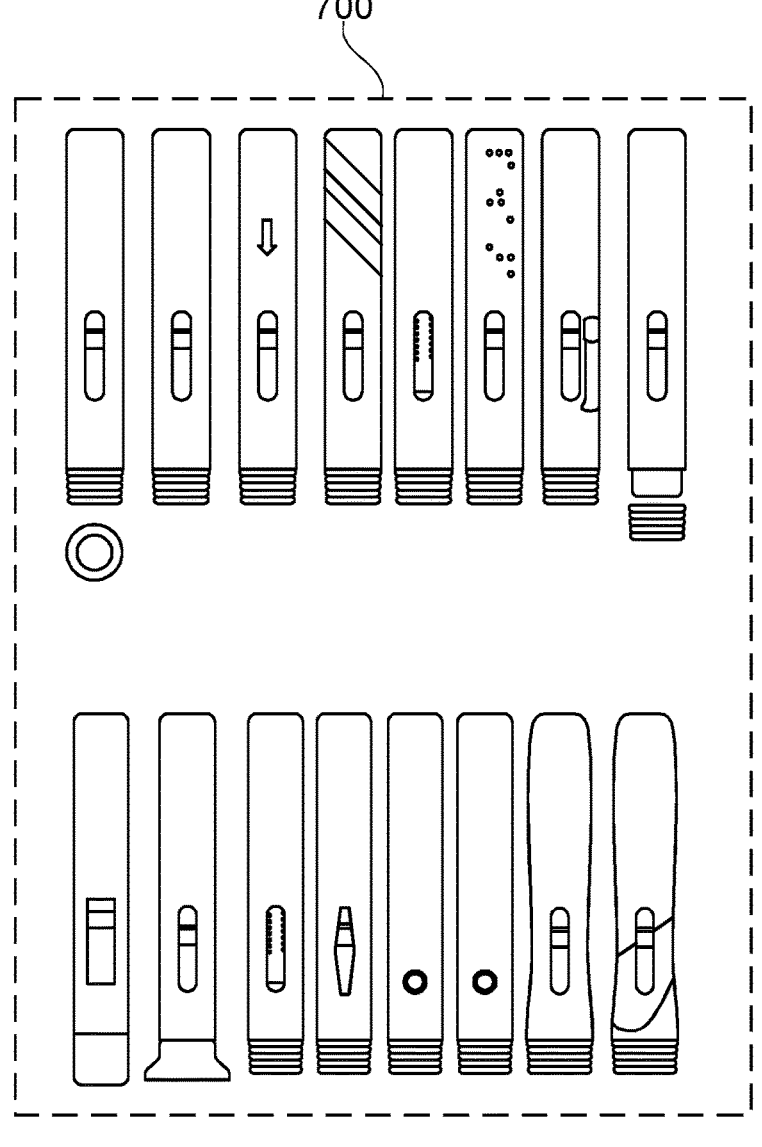
*Fig. 10*

METHOD OF MANUFACTURING A SUB-ASSEMBLY OF A MEDICAMENT DELIVERY DEVICE

CROSS-REFERENCE TO RELATED APPLICATIONS

The present application is a U.S. National Phase Application pursuant to 35 U.S.C. § 371 of International Application No. PCT/EP2022/071828 filed Aug. 3, 2022, which claims priority to EP patent application Ser. No. 21/190,457.8 filed Aug. 9, 2021. The entire disclosure contents of these applications are herewith incorporated by reference into the present application.

TECHNICAL FIELD

The present disclosure generally relates to a method of manufacturing a medicament delivery device, and particularly to the method of manufacturing a sub-assembly of a medicament delivery device.

BACKGROUND

Standardizing components of medicament delivery devices can provide the benefit of cost reduction, reducing the complexity of manufacture, and increasing the robustness of the manufactured product. However, medicament delivery devices may be used to deliver many different drugs having varying viscosities and/or desired volumes. Therefore, different technical requirements need to be fulfilled at the same time and normally will require customization of the medicament delivery devices. As a result, the manufacturing of these devices can be complex and expensive due to the need to properly identify suitable components that can effectively deliver the medicament to the user.

It has been appreciated, that solutions for providing a method of manufacturing/assembling sub-assembly of a medicament delivery device. Therefore, a less complex and low-priced method of manufacturing/assembling sub-assembly of a medicament delivery device could be advantageous.

SUMMARY

The invention is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", or "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

There is hence provided a method of manufacturing a sub-assembly of a medicament delivery device, the method comprising: identifying one or more standardized components for the sub-assembly of the medicament delivery device from a group of standardized components; the group of standardized components comprises at least one of a group of interchangeable plunger rods and a group of interchangeable delivery member guards; the plunger rods in the group of interchangeable plunger rods have a structural and/or dimensional difference relative to one another; and the delivery member guards in the group of interchangeable delivery member guards have a structural and/or dimensional difference relative to one another; providing the identified one or more standardized components; providing a universal powerpack for the medicament delivery device; and assembling the sub-assembly of the medicament delivery device using the universal powerpack, and the identified one or more standardized components.

Preferably, according to another embodiment, when the group of standardized components comprises a group of interchangeable plunger rods; the step of identifying one or more standardized components for the sub-assembly of the medicament delivery device from a group of standardized components comprises the steps of: identifying a length of a plunger rod; and including the plunger rod with the identified length from the group of plunger rods into the identified one or more standardized components.

Preferably, according to another embodiment, when the group of standardized components comprises a group of interchangeable delivery member guards; the step of identifying one or more standardized components for the sub-assembly of the medicament delivery device from a group of standardized components comprises the steps of: identifying a length of a delivery member guard; and including the delivery member guard with the identified length from the group of delivery member guards as one of the identified one or more standardized components.

Preferably, according to another embodiment, the group of standardized components comprises a group of housings; the step of identifying one or more standardized components for the sub-assembly of the medicament delivery device from a group of standardized components comprises the steps of: identifying a type of housing; and including the identified type of housing from the group of housings into the identified one or more standardized components.

Preferably, according to another embodiment, the group of standardized components comprises at least one of a group of interchangeable plunger rod springs and a group of interchangeable delivery member guard springs; the plunger rod springs in the group of interchangeable plunger rod springs comprise a structural and/or dimensional difference relative to one another; and the delivery member guard springs in the group of interchangeable delivery member guard springs comprise a structural and/or dimensional difference relative to one another.

Preferably, according to another embodiment, when the group of standardized components comprises a group of interchangeable plunger rod springs; the step of identifying one or more standardized components for the sub-assembly of the medicament delivery device from a group of standardized components comprises the steps of: identifying a value for the force of a plunger rod spring; and including the plunger rod spring with the identified value for the force from the group of plunger rod springs into the identified one or more standardized components.

Preferably, according to another embodiment, when the group of standardized components comprises a group of interchangeable medicament delivery member guard springs; the step of identifying one or more standardized components for the sub-assembly of the medicament delivery device from a group of standardized components comprises the steps of: identifying a value for the force of a delivery member guard spring; and including the delivery member guard spring with the identified value for the force from the group of delivery member guard springs into the identified one or more standardized components.

Preferably, according to another embodiment, the group of standardized components comprises a group of cap assemblies.

Preferably, according to another embodiment, the group of cap assemblies comprises two types of cap assemblies; one of the two types of cap assemblies comprises a delivery member shield remover; and the other one of the two types of cap assemblies comprises a delivery member.

Preferably, according to another embodiment, the step of identifying one or more standardized components for the sub-assembly of the medicament delivery device from a group of standardized components comprises the steps of: identifying, based on whether a predetermined medicament container of the medicament delivery device is integral with a delivery member, a cap assembly; and including the identified type of cap assembly from the group of cap assemblies into the identified one or more standardized components.

Preferably, according to another embodiment, the group of standardized components comprises a group of interchangeable medicament container holders; and medicament container holders in the group of interchangeable medicament container holders comprise a structural and/or dimensional difference relative to one another.

Preferably, according to another embodiment, the step of identifying one or more standardized components for the sub-assembly of the medicament delivery device from a group of standardized components comprises the steps of: identifying a width of a medicament container holder; and including the medicament container holder with the identified width from the group of medicament container holders into the identified one or more standardized components.

Preferably, according to another embodiment, the step of assembling the sub-assembly of the medicament delivery device using the universal powerpack and the identified one or more standardized components comprises the steps of: defining, based on at least one characteristic of the medicament delivery device, an initial position between the universal powerpack and the plunger rod of the identified one or more standardized components; and engaging the plunger rod of the identified one or more standardized components to the universal powerpack at the defined initial position.

Another aspect of the present disclosure provides a method of manufacturing a medicament delivery device, the method comprising: providing a medicament container; identifying, based on the provided medicament container, one or more standardized components for the medicament delivery device from a group of standardized components; the group of standardized components comprises at least one of a group of interchangeable plunger rods and a group of interchangeable delivery member guards; the plunger rods in the group of interchangeable plunger rods have a structural and/or dimensional difference relative to one another; and the delivery member guards in the group of interchangeable delivery member guards have a structural and/or dimensional difference relative to one another; providing the identified one or more standardized components; providing a universal powerpack for the medicament delivery device; and assembling the medicament delivery device using the universal powerpack, the medicament container, and the identified one or more standardized components.

Another aspect of the present disclosure provides a method of manufacturing a medicament delivery device, the method comprising: identifying a type of medicament container from two types of medicament containers, a first type of medicament container comprises a delivery member, and a second type of medicament container does not comprise delivery members; identifying, based on the identified type medicament container, a cap assembly; providing a universal powerpack for the medicament delivery device; and assembling the medicament delivery device using the universal powerpack, the identified medicament container, and the identified cap assembly.

Preferably, according to another embodiment, the medicament delivery device is an injection device, an inhalation device, or a medical sprayer.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

Embodiments of the inventive concept will now be described, by way of example only, with reference to the accompanying drawings, in which:

FIG. 2A schematically shows a side view of different medicament containers.

FIG. 2B schematically shows a side view of different housings.

FIGS. 3A-4B schematically show perspective views of a universal powerpack in different examples.

FIGS. 7A-7C schematically show perspective views of a part of the universal powerpack and the plunger rod in one example.

FIG. 10 schematically show an example approach for designing and manufacturing a medicament delivery device with the method of FIG. 1.

DETAILED DESCRIPTION

FIGS. 1-10 illustrate a method of manufacturing a medicament delivery device and a method of manufacturing a sub-assembly of a medicament delivery device. The method of manufacturing a medicament delivery device and the method of manufacturing a sub-assembly of a medicament delivery device comprise identifying at least one of standardized components for the medicament delivery device from a group of standardized components, components in the group have a structural and/or dimensional difference relative to one another; providing the identified at least one of standardized components; providing a universal power-pack 1; 1' for the medicament delivery device; assembling the medicament delivery device using the universal power-pack 1; 1', and the identified one or more of standardized components. The method of manufacturing a medicament delivery device further comprises a step of assembling the medicament delivery device using the universal powerpack 1; 1', the identified one or more of standardized components, and a medicament container. Furthermore, the method of manufacturing a medicament delivery device optionally comprises one or more steps of identifying a medicament; identifying, based on the identified medicament, a medicament container; filling the identified medicament container with the identified medicament; and providing the identified medicament container with the contained medicament. Preferably, the sub-assembly of the medicament delivery device is configured to comprise all components that can form a medicament delivery device except a medicament container with a contained medicament, e.g. a cartridge C (a medicament container without medicament delivery member) or a syringe S (a medicament container with medicament delivery member).

Figure 1:
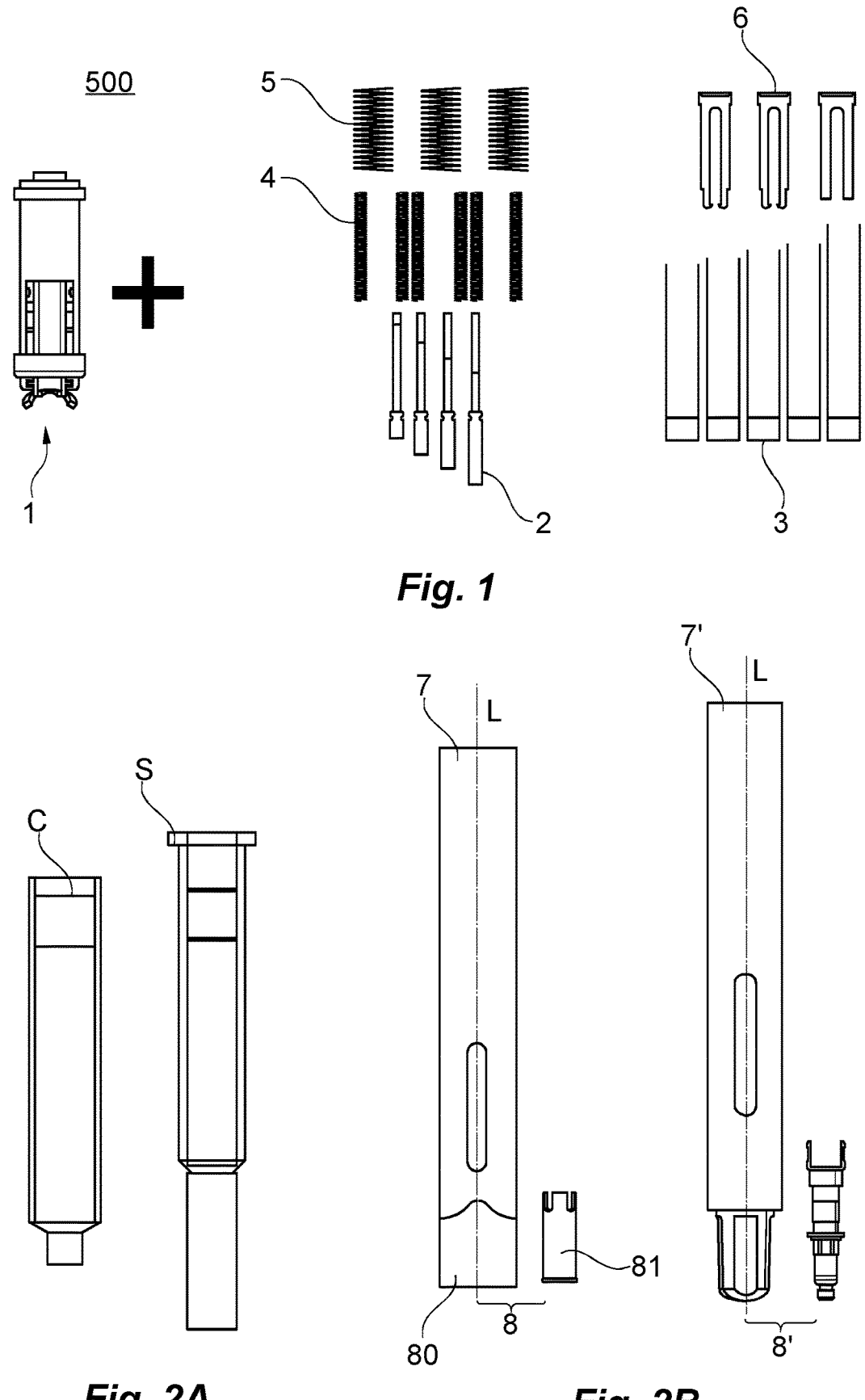
FIG. 1 schematically shows a side view of a set of standardized components of a medicament delivery device.

The method is configured to use certain numbers of standardized components to address different technical requirements regarding the characteristic of the medicament delivery devices (normally related to the characteristic of contained medicaments) with a universal powerpack, as shown by FIG. 1. Sub-assemblies of medicament delivery devices of the present disclosure can be used for, in a certain range, medicament delivery devices with different technical requirements. The structure and dimension of all components in one sub-assembly will be set in accordance with the range. For example, the range can be set with a combination of one or more factors of medicament delivery devices, such as delivering a medicament with a volume between 0.3 ml-3 ml; being compatible to a needle length between 12 mm-19.5 mm, when the medicament delivery device is an injector; and delivering a medicament with a viscosity less than 30 centipoise (cP). The method of the present disclosure can be used to manufacture multiple sub-assemblies of medicament delivery devices with different ranges being set.

The universal powerpack 1; 1' is configured to releasably hold a plunger rod of the sub-assembly of the medicament delivery device against a force of a plunger rod spring of the sub-assembly of the medicament delivery device. Generally, the set of components that performs the function as the universal powerpack is one of the key designs in a medicament delivery device, because such a set of components will normally impact certain factors of the performance of the medicament delivery device, such as a triggering force for initiating a medicament delivery operation, controlling of multiple shots of medicament delivery, and the capability of a long storage period of the medicament delivery device. Therefore, if one robust powerpack can be used for medicament delivery devices with different technical requirements regarding to medicaments of medicament delivery devices, the performance of those medicament delivery devices can be increased.

In one example, the universal powerpack 1; 1' comprises a powerpack housing 10; 100' a holder 11; 11', and a retainer 12; 12'. The powerpack housing 10; 100' extends along a longitudinal axis L between a proximal end and a distal end. The powerpack housing 10; 100' is configured to attach to a housing of the identified one or more of standardized components. The holder 10; 100' comprises a distally directed surface 111; 111' for releasably engaging with a proximally directed surface 21a, 21b; 21' of a plunger rod 2; 2' of the sub-assembly of the medicament delivery device. The retainer 12; 12' is configured to movably engage with the holder 11; 11' and to engage with a delivery member guard of the sub-assembly of the medicament delivery device. Optionally, the universal powerpack comprises a flexible arm 13; 13' arranged on a proximal end of the powerpack housing for supporting a medicament container of the medicament delivery device.

The key factor of forming the universal powerpack will be to isolate the universal powerpack from other components of the medicament delivery device so that a certain variation of structure and/or dimension of other components of a medicament delivery device can all be used with the same universal powerpack to form a medicament delivery device. In one example, the medicament delivery device is configured to be triggered by a linear movement of the medicament delivery member guard relative to the powerpack housing 10; 100'. In this example, a distal portion of the delivery member guard will abut on a proximally directed surface of the retainer when the sub-assembly of the medicament delivery device has been assembled. Therefore, when the medicament delivery member guard acts on the retainer 12; 12', the delivery member guard will also move the retainer 12; 12' to release the plunger rod from the holder 11; 11. The structure of different the medicament delivery member guard can be varied.

Figures 3A, 3B, 4A, 4B:
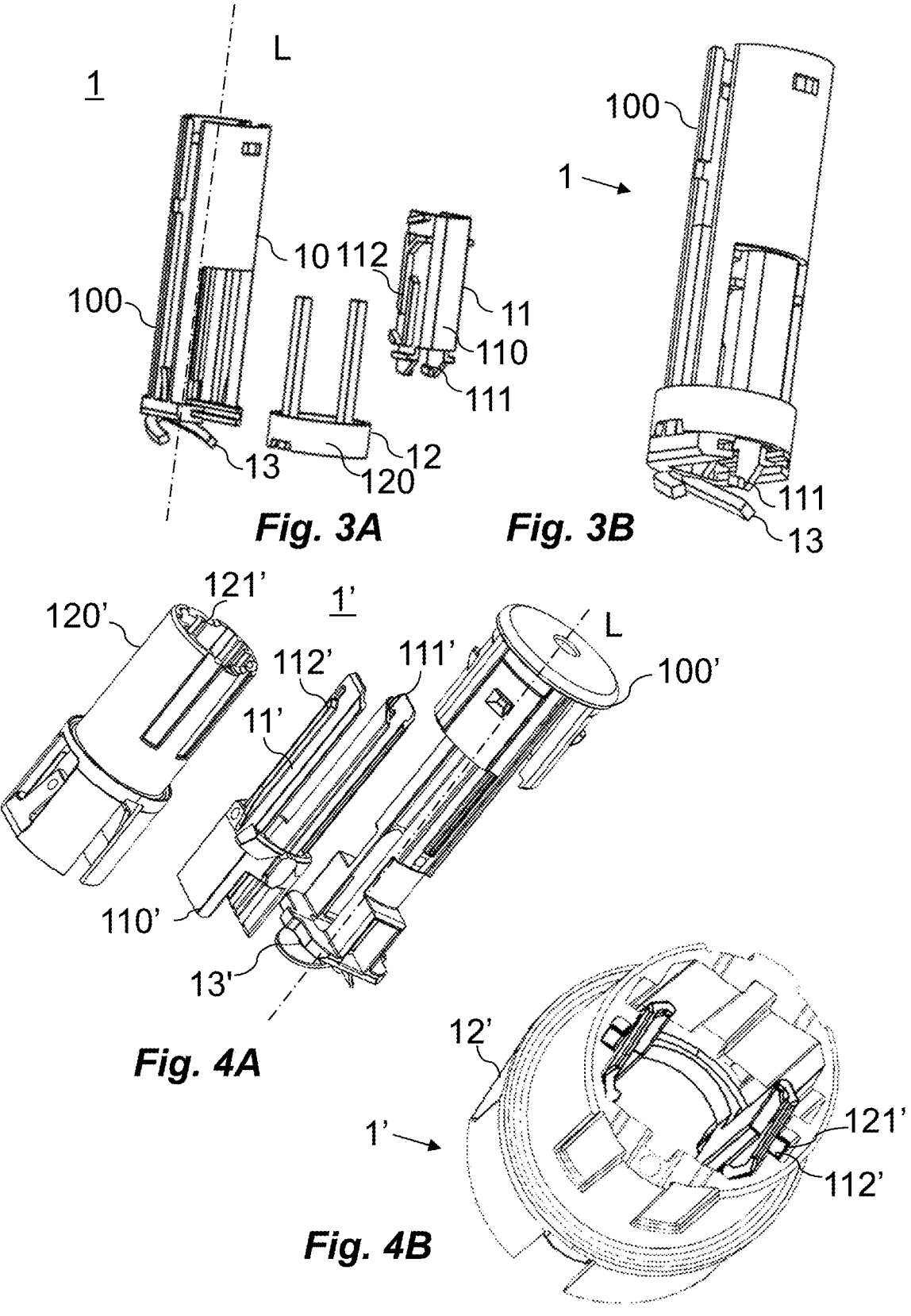

For increasing the compatibility of the universal powerpack 1; 1', in one example, the holder 11 comprises a guide track 112, preferably arranged on an inner/outer surface of a holder body 110, and the retainer 12 comprises a protrusion 120a extending from a retainer body 120, and the protrusion 120a is configured to follow the guide track 112, as shown in FIGS. 3A-B. The guide track 112 comprises a start position 112a, an intermediate position 112b and a release position 112c, as shown in FIG. 7A. The movement of the protrusion 120a from the start position 112a to the release position 112c is configured to move the holder 11 relative to the plunger rod, e.g. to rotate or linearly move in a direction transverse to the longitudinal axis L. The relative movement between the holder 11 and the plunger rod disengages the holder 11 from the plunger rod. The length of the intermediate position 112b is configured to compensate for the different length of the medicament delivery member guards. In another example, the interface formed between the distally directed surface 111' of the holder 11' and the proximally directed surface 21a' of the plunger rod 2' is a ramp surface. The holder 11' comprises a rib 112' extending along the longitudinal axis L, and the retainer 12' comprises a slot 121'. In this example, the force from the plunger rod spring can move the holder 11' in the direction transverse to the longitudinal axis, due to the ramp interface between the holder 11' and the plunger rod 2'. The rib 112' of the holder 11' is configured to be received within the slot 121' of the retainer 12', so that the holder 11' cannot be moved under the force of the plunger rod spring. The delivery member guard is configured to move the retainer 12' relative to the holder 11'. Once the slot 121' of the retainer 12' disengages from the rib 112' of the holder 11', the holder 11' can be moved to release the plunger rod 2' by the force of the plunger rod spring. In this example, the length of the rib 112' and/or the slot 121' is configured to compensate for different lengths of medicament delivery member guard.

Furthermore, because the holder is movable relative to the delivery member guard, the holder may comprise a set of member guard lockout arrangements, e.g. a ratchet, for locking the delivery member guard after use of the medicament delivery device.

It should be noted that the universal powerpacks 1; 1' for the sub-assemblies of the medicament delivery devices can be formed in any suitable way. However, all universal powerpacks 1 used in the method of manufacturing any one type of sub-assemblies of the medicament delivery devices are geometrically identical to each other.

Figures 5A, 5B, 6:
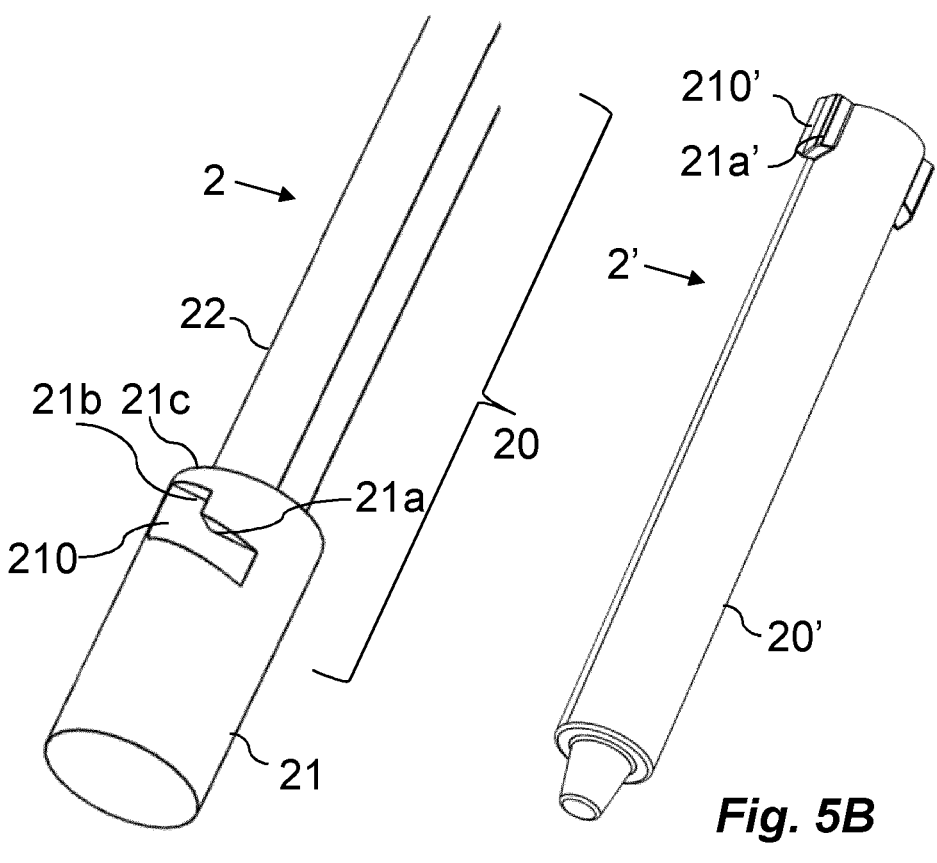
FIGS. 5A-5B schematically show perspective views of a plunger rod in different examples.
FIG. 6 schematically shows a perspective view of a plunger rod with a plunger rod spring.

The group of standardized components comprises a group of interchangeable plunger rods 2; 2' and/or a group of interchangeable delivery member guards 3. In one example, each plunger rod of the group of interchangeable plunger rods comprises the proximally directed surface 21a, 21b; 21'. The proximally directed surface 21a, 21b can comprise two or more contiguously connected, stairway-like proximally directed surfaces 21a, 21b, formed by a shape of a recess 210, as shown in FIG. 5A, so that the plunger rod 2 can be used with a medicament delivery device that will only perform one shot of medicament delivery operation or one or more sequential shots of medicament delivery operation before delivering the medicament to a user, e.g. a priming shot or a mixing shot. It should be noted that, alternatively, the proximally directed surface 21a, 21b can be formed by a protrusion. Furthermore, the two or more contiguously connected, stairway-like proximally directed surfaces 21a, 21b can be replaced by two or more contiguously connected, stairway-like distally directed surfaces of the holder.

Each plunger rod of the group of interchangeable plunger rods 2' may comprise a tubular body 20' for receiving a plunger rod spring, as shown in FIG. 5B, so that the medicament delivery device will be compact. Alternatively, each plunger rod of the group of interchangeable plunger rods 2 may comprise a body 20 with a proximal body part 21 and a distal body part 22. The proximal body part 21 is configured to directly contact a stopper of the medicament container, therefore, the proximal body part 21 of the plunger rod 2 may comprise a flat surface for contacting the stopper of the medicament container. Optionally, the recess 210 or protrusion for defining the proximally directed surface 21a, 21b can be arranged on an outer surface 210 of the proximal body part. The distal body part 22 can be formed with a narrower diameter than the proximal body part 21, or formed by two or more elongated arms. Therefore, a distal end of the proximal body 21 can be used to connect to one end of the plunger rod spring.

The general shapes of all plunger rods in the group of interchangeable plunger rods should be similar; however, plunger rods in the group of interchangeable plunger rods have a structural and/or dimensional difference relative to one another. The chosen dimension and/or structure of the universal powerpack 1; 1' will define the range of dimensional and/or structural variation of the plunger rods in the group of plunger rods 2. Similarly, the general shapes of all delivery member guards in the group of interchangeable delivery member guards should be similar; but delivery member guards in the group of interchangeable delivery member guards comprise a structural and/or dimensional difference relative to one another. The chosen dimension and/or structure of the universal powerpack 1; 1' will define the range of dimensional and/or structural variation of the delivery member guards in the group of delivery member guards.

For example, in the group of plunger rods 2 and/or the group of delivery member guards, the grouped components have different length. It can be achieved by either manufacturing a number of components in each group with different length, or manufacturing components in each group with the same length and manufacturing a length adapter with a different length that can be attached to the grouped components.

Therefore, the step of identifying one or more of standardized components for the sub-assembly of the medicament delivery device from a group of standardized components comprises a step of identifying a length of a plunger rod. The length of a plunger rod normally dependent on the volume of medicament contained within the medicament container. Further, the step of identifying one or more of standardized components for the sub-assembly of the medicament delivery device from a group of standardized components comprises steps of identifying a length of a delivery member guard. The length of a delivery member guard is normally dependent on the length of a medicament delivery member, and/or an injection depth (when the medicament delivery device is an injection device), and/or whether a medicament delivery device has a function of automatic penetration/retraction (when the medicament delivery device is an injection device). Once the length of a plunger rod and/or a medicament delivery member guard has been identified, the step of identifying one or more of standardized components for the sub-assembly of the medicament delivery device from a group of standardized components comprises a step of including the plunger rod with the identified length from the group of plunger rods and/or the delivery member guard with the identified length from the group of delivery member guards into the identified one or more of standardized components.

The group of standardized components may also comprise at least one of a group of interchangeable plunger rod springs 5, a group of interchangeable delivery member guard springs 4, a group of housings 7, a group of cap assemblies 8, 8', and a group of interchangeable medicament container holders 6.

Similarly, plunger rod springs in the group of interchangeable plunger rod springs and delivery member guard springs in the group of interchangeable delivery member guard springs have a structural and/or dimensional difference relative to one another in the same group. The difference of the structure and/or dimension of springs normally can be used to set a different value for the force, e.g. how much Newton (N) force can be outputted. What force is required is normally dependent on the viscosity of the contained medicament of the medicament delivery device. The value for the force of the delivery member guard is sometimes related to a triggering force of the medicament delivery device. The step of identifying one or more of standardized components for the medicament delivery device from a group of standardized components may comprise steps of identifying a value for the force of a plunger rod spring; and/or identifying a value for the force of a delivery member guard spring; and including the plunger rod spring with the identified value for the force from the group of plunger rod springs, and/or the delivery member guard spring with the identified value for the force from the group of delivery member guard springs into the identified one or more of standardized components. Furthermore, all medicament container holders in the group of interchangeable medicament container holders may be formed in shapes that are generally similar to one another; but medicament container holders in the group of interchangeable medicament container holders comprise a structural and/or dimensional difference relative to one another. For example, each medicament container holder may have a different width for tolerating a different volume of medicament container. The step of identifying one or more of standardized components for the sub-assembly of the medicament delivery device from a group of standardized components comprises steps of identifying a width of a medicament container holder; and including the medicament container holder with the identified width from the group of medicament container holders into the identified one or more of standardized components. Alternatively, the container holders may be formed with a different structure specifically for containing a syringe S or a structure of a cartridge.

In a preferred example, the delivery member guard spring is configured to abut on a distally directed surface of the retainer 12; 12' of the universal powerpack at one end, and abut, directly or indirectly, on a proximally directed surface of the powerpack housing 10; 100'. The retainer 12; 12' can be positioned at a before-trigger position, thus the universal powerpack can be prevented from accidentally releasing the engaged plunger rod.

All housings in the group of housings 7; 7' extend along the longitudinal axis L between a proximal end and a distal end. In a preferred example, the group of housings 7; 7' only comprises two housings 7; 7'. One of the two housings is configured to use with a cartridge, and the other one of the two housings is configured to use with a syringe.

Figures 8A, 8B, 9A, 9B, 9C:
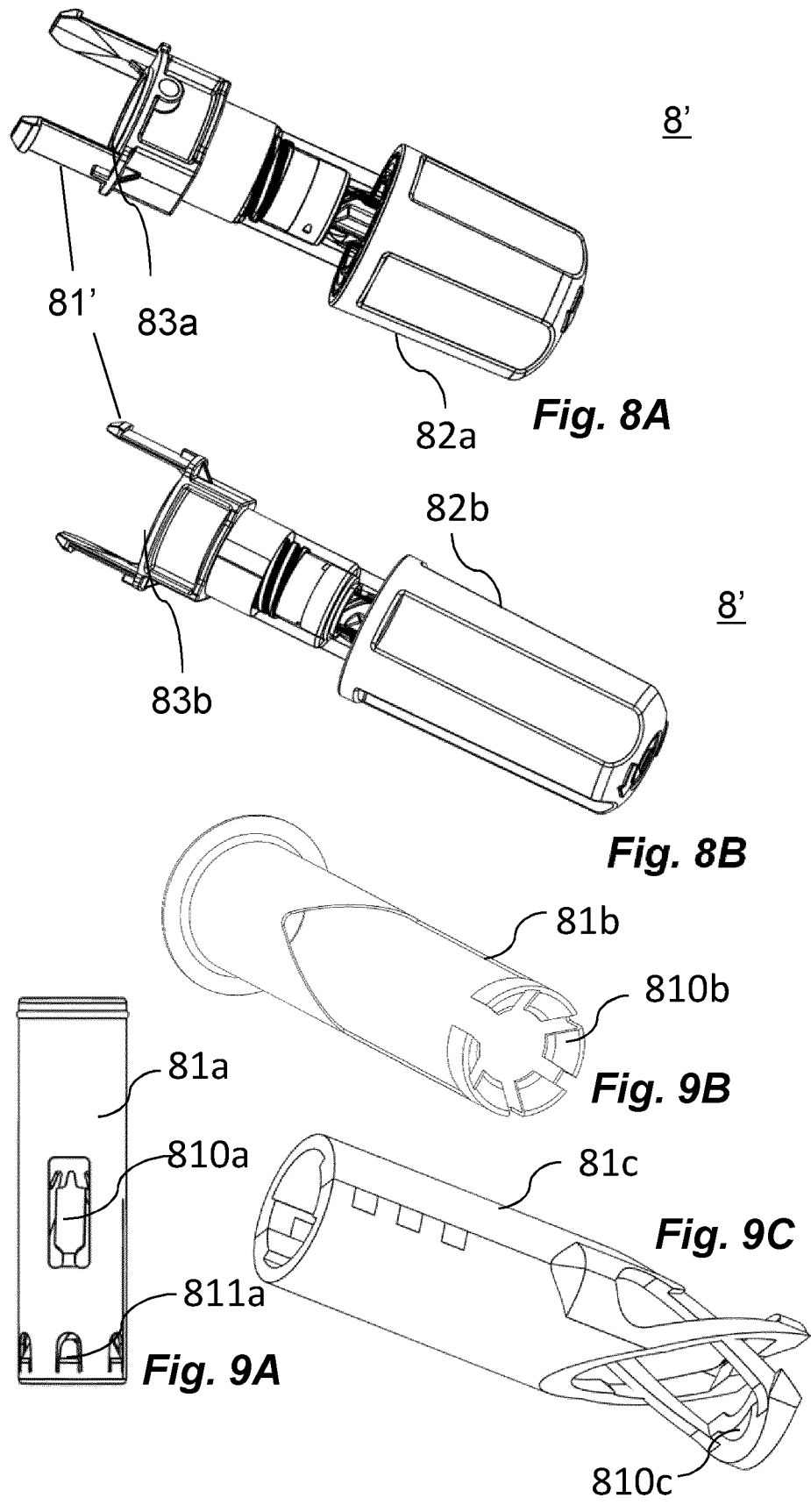
FIGS. 8A-8B schematically show perspective views of cap assemblies in a group of cap assemblies.
FIGS. 9A-9C schematically show perspective views of a delivery member shield remover in different example.

Further, in a preferred example, the group of cap assemblies 8; 8' only comprises two types of cap assemblies, namely, all cap assemblies in the group of cap assemblies 8; 8' can be categorized into two different types, based on the different comprised elements. In this example, there are certain numbers of cap assemblies that can be categorized in one type; cap assemblies that are categorized in the same type are functionally identical, and are differently dimensioned relative to one another. In a preferred example, one of the two types of cap assemblies is configured to use with a cartridge, and the other one of the two types of cap assemblies is configured to use with a syringe. As shown in FIGS. 8A-B, each of the cap assemblies 8' that are configured to use with cartridges comprise delivery members (detailed description of the technology of a suitable cap assembly can be found in certain prior arts, e.g. WO2009/150078). In a preferred example, cap assemblies that are categorized in the type for cartridges may have different lengths but otherwise the same structure to one another, with the length being dependent on the length of the delivery member. For example, the length of the delivery members of the cap assemblies 8' for cartridges may be different, so the length of the cover caps 82*a*; 82*b* of each categorized cap assemblies 8' will also be different. In a preferred example, the cap assembly 8' for a cartridge is independent of other components of the medicament delivery device. Preferably, the cap assembly 8', in this example, comprises a fastener 81' is configured to snap-fit on the housing 7' for a cartridge. In this example, the housing 7' comprises a counter fastener for fitting with the fastener 81'. It should be noted that, in this example, a container holder is an optional component, because the cap assembly 8' for a cartridge can also provide a support function by a support surface. On the other hand, the counter fastener can be arranged on a container holder for the cartridge. On the other hand, the other type of the cap assemblies for a syringe doesn't comprise a delivery member, instead, each of the categorized cap assemblies 8 for a syringe comprises a delivery member shield remover 81*a*; 81*b*; 81*c*, as shown in FIGS. 9A-C. Because a syringe means a medicament container with a delivery member shield, the delivery member of the syringe is always sealed by a delivery member shield before a medicament delivery operation to maintain a sterile environment. The delivery member shield 81*a*; 81*b*; 81*c* should be formed with a structure that can remove both a flexible delivery member shield and/or a rigid delivery member shield, for example, the delivery member shield 81*b*; 81*c*, which as shown in FIGS. 9B-C is configured to grip on a distal end of the delivery member shield by a gripper 810*b*; 810*c*; and the delivery member shield 81*a*, as shown in FIG. 9A comprises one type of gripper 810*a* for gripping the flexible delivery member shield, and the other type of gripper 811*a* for gripping the rigid delivery member shield. It should be noted that the delivery member shield 81*a*; 81*b*; 81*c* can be formed in any suitable way. Further, there could be several sub-assemblies of medicament delivery devices. However, there should be only one type of delivery member shield 81*a*; 81*b*; 81*c* used in the manufacture process for manufacturing one batch of sub-assemblies of the medicament delivery device. The type of cap assemblies 8 for a syringe may be formed with one length that can tolerate delivery members with different length; or be a sub-group of cap assemblies 8 for syringes, that comprises cap assemblies with similar shapes but with different length regarding different delivery members with different length.

The step of assembling the sub-assembly of the medicament delivery device using the universal powerpack and the identified one or more of standardized components comprises steps of defining, based on one or more characteristic of the medicament delivery device, an initial position between the holder 11; 11' of the universal powerpack and the plunger rod 2; 2' of the identified one or more of standardized components; and engaging the proximally directed surface of the plunger rod 2; 2' of the identified one or more of standardized components to the distally directed surface of the holder at the defined initial position. For example, if there is a demand for priming or mixing two contained medicaments, the plunger rod 21 may engage with the holder 11 at one of the two stairway-like proximally directed surfaces 21*a*, as the initial position. On the other hand, if the medicament delivery device will need to perform one medicament delivery operation to deliver the medicament to the user, the plunger rod 21 may engage with the holder 11 at the other one of the two stairway-like proximally directed surfaces 21*b*, as the initial position.

Similarly, in the example that the holder 11 of the universal powerpack 1; 1' comprises the holder body 110 and the guide track 112 on, preferably, an outer surface of the holder body 110, the step of assembling the sub-assembly of the medicament delivery device using the universal powerpack and the identified one or more of standardized components comprises steps of identifying, based on at least one characteristic of the medicament delivery device, a location on the guide track 112 of the holder 11 of the universal powerpack 1; 1'; and locating the protrusion 120*a* of the retainer 12 of the universal powerpack 1; 1' at the identified location of the guide track 112 of the holder 11 of the universal powerpack 1; 1'. For example, if there is a demand for priming or mixing two contained medicaments, instead of being located at the start position 112*a*, the protrusion 120*a* can be located at a first extra position 112*d*, so that when the retainer 12 moves in the proximal direction, e.g. by gravity, by being pulled or by being biased by the medicament delivery member guard spring together with the movement of the medicament delivery member guard once the cap assembly 8; 8' has been removed. The protrusion 120a will move to the start position 112a through a ramp surface 112e, and thereby rotate or linearly move the holder 11 to release the plunger rod 2 from one of the stairway-like proximally directed surfaces 21a to the other stairway-like proximally directed surfaces 21b.

Once the sub-assembly of the medicament delivery device has been assembled, the powerpack housing 10; 100' will be fixed to the housing of the identified one or more of standardized components, the delivery member guard of the identified one or more of standardized components will be telescopic relative to the powerpack housing 10; 100', and the cap assembly 8; 8' of the identified one or more of standardized components will be releasably attached to the proximal end of the housing 10; 100' and/or the delivery member guard.

Furthermore, another aspect of the present disclosure provides a method of manufacturing a medicament delivery device, based on the above-mentioned method of manufacturing. In this example, the method comprises providing a medicament container; identifying, based on the provided medicament container, one or more standardized components for the medicament delivery device from a group of standardized components. For example, a dimension of the medicament container, a volume and/or viscosity of a medicament contained within the medicament container, and/or a length of a delivery member integral to the medicament container can be the basis for identifying one or more standardized components for the medicament delivery device from a group of standardized components. As mentioned above, the group of standardized components comprises at least one of a group of interchangeable plunger rods and a group of interchangeable delivery member guards; the plunger rods in the group of interchangeable plunger rods have a structural and/or dimensional difference relative to one another; and the delivery member guards in the group of interchangeable delivery member guards have a structural and/or dimensional difference relative to one another. The method comprises steps of providing the identified one or more standardized components; providing a universal powerpack for the medicament delivery device; and assembling the medicament delivery device using the universal powerpack, the medicament container, and the identified one or more standardized components.

Moreover, another aspect of the present disclosure provides another method of manufacturing a medicament delivery device, the method comprising: identifying a type of medicament container from two types of medicament containers, a first type of medicament container comprises a delivery member, e.g. a syringe, and a second type of medicament container does not comprise delivery members, e.g. a cartridge; identifying, based on the identified type medicament container, a cap assembly. The cap assembly should be identified from the group of cap assemblies 8; 8' as mentioned above. For example, if the first type of medicament container is identified, the cap assembly 8 is configured to use with a syringe, as described above, should be identified. On the other hand, if the second type of the medicament container is identified, the cap assembly 8' is configured to use with a cartridge, as described above, should be identified. The method comprises steps of providing a universal powerpack for the medicament delivery device; and assembling the medicament delivery device using the universal powerpack, the identified medicament container, and the identified cap assembly.

An exemplified design and manufacture blueprint related to all methods of the present disclosure is shown in FIG. 10. The design and manufacture blueprint in this example is formed by three design and phase 500 (as shown in FIG. 1), 600, 700. The first phase is aiming to provide a simple, robust and low-cost platform medicament delivery device by using the sub-assembly of the medicament delivery device. The second phase 600 aims to provide few selectable functions that can be achieved by simply attaching components on the sub-assembly of the medicament delivery device. The third phase 700 aims to provide an optional customized feature that cannot be standardized, e.g. due to the regulatory requirement, such as labels or extra shells.

It should be noted that, depending on the set range of different sub-assemblies, the universal powerpack may further comprise at least one of a plunger rod, a plunger rod spring, medicament delivery guard spring, a medicament delivery member guard and any other suitable components. The more components have been included as a part of the universal powerpack, the less flexibility is provided within the design.

It should be noted that, to manufacture a sub-assembly of a medicament delivery device, usually there will be only one component selected from each group of interchangeable components. For example, usually there will be only one interchangeable plunger rod identified from the group of interchangeable plunger rods, and/or there will be only one interchangeable delivery member guard identified from the group of interchangeable delivery member guards. This is also the case for identifying a plunger rod spring, a delivery member guard spring, and a cap assembly. However, there are various type of medicament delivery devices. For example, for some medicament delivery devices, two plunger rods and two plunger rod springs can be required, e.g. for delivering two doses or for performing a mixing operation of multiple contained medicaments and the medicament delivery operation. Therefore, how many, and which components should be identified from the groups of interchangeable components are dependent on the design of the medicament delivery devices.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A method of manufacturing a sub-assembly of a medicament delivery device, the method comprising:

identifying one or more standardized components for the sub-assembly of the medicament delivery device from a group of standardized components, wherein the group of standardized components comprises at least one of a group of interchangeable plunger rods, a group of interchangeable delivery member guards, and at least one of a group of interchangeable plunger rod springs and a group of interchangeable delivery member guard springs, wherein the plunger rods in the group of interchangeable plunger rods have a structural and/or dimensional difference relative to one another, wherein the delivery member guards in the group of interchangeable delivery member guards have a structural and/or dimensional difference relative to one another, and wherein the plunger rod springs comprise one or more distinct force values;

identifying, based on the other standardized components identified, a force value for a plunger rod spring;

including the plunger rod spring with the identified force value as one of the identified one or more standardized components;

providing the identified one or more standardized components;

providing a universal powerpack for the medicament delivery device; and assembling the sub-assembly of the medicament delivery device using the universal powerpack, and the identified one or more standardized components.

2. The method according to claim 1, wherein the group of standardized components comprises a group of interchangeable plunger rods, and wherein the step of identifying one or more standardized components for the sub-assembly of the medicament delivery device from a group of standardized components comprises the steps of:

identifying a length of a plunger rod; and including the plunger rod with the identified length from the group of plunger rods into the identified one or more standardized components.

3. The method according to claim 1, wherein the group of standardized components comprises a group of interchangeable delivery member guards, and wherein the step of identifying one or more standardized components for the sub-assembly of the medicament delivery device from a group of standardized components comprises the steps of:

identifying a length of a delivery member guard; and including the delivery member guard with the identified length from the group of delivery member guards as one of the identified one or more standardized components.

4. The method according to claim 1, wherein the group of standardized components comprises a group of housings, and wherein the step of identifying one or more standardized components for the sub-assembly of the medicament delivery device from a group of standardized components comprises the steps of:

identifying a type of housing; and including the identified type of housing from the group of housings into the identified one or more standardized components.

5. The method according to claim 1, wherein the group of standardized components comprises at least one of a group of interchangeable delivery member guard springs, wherein the delivery member guard springs in the group of interchangeable delivery member guard springs comprise a structural and/or dimensional difference relative to one another.

6. The method according to claim 5, wherein the group of standardized components comprises a group of interchangeable medicament delivery member guard springs, and wherein the step of identifying one or more standardized components for the sub-assembly of the medicament delivery device from a group of standardized components comprises the steps of:

14 identifying a value for the force of a delivery member guard spring; and including the delivery member guard spring with the identified value for the force from the group of delivery member guard springs into the identified one or more standardized components.

7. The method according to claim 1, wherein the group of standardized components comprises a group of cap assemblies.

8. The method according to claim 7, wherein the group of cap assemblies comprises two types of cap assemblies, wherein one of the two types of cap assemblies comprises a delivery member shield remover, and wherein the other one of the two types of cap assemblies comprises a delivery member.

9. The method according to claim 8, wherein the step of identifying one or more standardized components for the sub-assembly of the medicament delivery device from a group of standardized components comprises the steps of:

identifying, based on whether a predetermined medicament container of the medicament delivery device is integral with a delivery member, a cap assembly; and including the identified type of cap assembly from the group of cap assemblies into the identified one or more standardized components.

10. The method according to claim 9, wherein the group of standardized components comprises a group of interchangeable medicament container holders, and wherein medicament container holders in the group of interchangeable medicament container holders comprise a structural and/or dimensional difference relative to one another.

11. The method according to claim 10, wherein the step of identifying one or more standardized components for the sub-assembly of the medicament delivery device from a group of standardized components comprises the steps of:

identifying a width of a medicament container holder; and including the medicament container holder with the identified width from the group of medicament container holders into the identified one or more standardized components.

12. The method according to claim 1, wherein the step of assembling the sub-assembly of the medicament delivery device using the universal powerpack and the identified one or more standardized components comprises the steps of:

defining, based on at least one characteristic of the medicament delivery device, an initial position between the universal powerpack and the plunger rod of the identified one or more standardized components; and engaging the plunger rod of the identified one or more standardized components to the universal powerpack at the defined initial position.

* * * * *